United States Patent
Ramachandran et al.

(10) Patent No.: US 10,327,916 B2
(45) Date of Patent: Jun. 25, 2019

(54) IMPACT ABSORBING PAD

(71) Applicant: Howmedica Osteonics Corp., Mahwah, NJ (US)

(72) Inventors: Rahul Ramachandran, Madison, NJ (US); Dalyssa Hernandez, Valhalla, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 515 days.

(21) Appl. No.: 14/790,439

(22) Filed: Jul. 2, 2015

(65) Prior Publication Data

US 2016/0000579 A1    Jan. 7, 2016

Related U.S. Application Data

(60) Provisional application No. 62/020,486, filed on Jul. 3, 2014.

(51) Int. Cl.

| *A61F 2/38* | (2006.01) |
|---|---|
| *A61F 2/46* | (2006.01) |
| *A61B 17/92* | (2006.01) |
| *A61F 2/30* | (2006.01) |
| *A61B 17/00* | (2006.01) |

(52) U.S. Cl.
CPC ............ *A61F 2/4603* (2013.01); *A61B 17/92* (2013.01); *A61F 2/461* (2013.01); *A61B 2017/00526* (2013.01); *A61B 2017/922* (2013.01); *A61F 2/389* (2013.01); *A61F 2002/30718* (2013.01); *A61F 2002/4623* (2013.01); *A61F 2002/4681* (2013.01)

(58) Field of Classification Search
CPC ..... A61F 2/389; A61F 2/3872; A61B 17/8028
See application file for complete search history.

(56) References Cited

U.S. PATENT DOCUMENTS

| 4,863,538 A | 9/1989 | Deckard |
|---|---|---|
| 4,944,817 A | 7/1990 | Bourell et al. |
| 5,017,753 A | 5/1991 | Deckard |
| 5,076,869 A | 12/1991 | Bourell et al. |
| 5,358,525 A | 10/1994 | Fox et al. |
| 6,336,941 B1 | 1/2002 | Subba Rao et al. |
| 6,679,967 B1 | 1/2004 | Carroll, III et al. |
| 6,875,235 B2 | 4/2005 | Ferree |

(Continued)

OTHER PUBLICATIONS

Page 59 of DePuySynthes / Joint Reconstruction. The base protector shown on p. 59 was on sale at least one year prior to the priority date of the application, <http://www.gsortho.org/files/attune_surgical_technique.pdf>.

*Primary Examiner* — Olivia C Chang
(74) *Attorney, Agent, or Firm* — Lerner, David, Littenberg, Krumholz & Mentlik, LLP (57) ABSTRACT

Various embodiments of an impact absorbing pad are disclosed herein. Each pad is configured to protect a load bearing surface of an implant from damage when the implant is implanted. Each pad may have an attachment portion that allows the pad to be attached to the load bearing surface. An impactor tool may also be attached to the load bearing surface and utilized the drive a portion of the implant into a bone cavity. The pad may be removed by hand, removed with the tool, or implanted with the implant. Related systems and methods for using and making the pad are also disclosed.

17 Claims, 5 Drawing Sheets

(56) References Cited

U.S. PATENT DOCUMENTS

| | | | |
|---|---|---|---|
| 7,179,295 B2 | 2/2007 | Kovacevic | |
| 7,288,326 B2 | 10/2007 | Elzey et al. | |
| 7,491,235 B2 | 2/2009 | Fell | |
| 7,513,344 B2 | 4/2009 | Toccalino et al. | |
| 7,537,664 B2 | 5/2009 | O'Neill et al. | |
| 7,991,599 B2 | 8/2011 | Linder-Ganz et al. | |
| 8,518,121 B2 | 8/2013 | Metzger et al. | |
| 8,532,783 B2 | 9/2013 | Zimmerling et al. | |
| 8,747,479 B2 | 6/2014 | McShane et al. | |
| 2002/0017805 A1 | 2/2002 | Carroll et al. | |
| 2004/0024460 A1 | 2/2004 | Ferree | |
| 2006/0064169 A1 | 3/2006 | Ferree | |
| 2009/0075026 A1 | 3/2009 | Vito et al. | |
| 2009/0125115 A1* | 5/2009 | Popoola | A61F 2/38 623/20.14 |
| 2009/0275945 A1* | 11/2009 | Makower | A61B 17/58 606/60 |
| 2011/0046735 A1* | 2/2011 | Metzger | A61F 2/3868 623/14.12 |
| 2013/0006370 A1* | 1/2013 | Wogoman | A61F 2/4684 623/20.16 |
| 2013/0020733 A1 | 1/2013 | Berger | |
| 2013/0071609 A1 | 3/2013 | Masse et al. | |
| 2014/0364955 A1 | 12/2014 | Smith | |
| 2015/0202048 A1* | 7/2015 | Roisin | A61F 2/389 623/20.32 |
| 2016/0076619 A1 | 3/2016 | Cormier et al. | |
| 2016/0327113 A1 | 11/2016 | Shelley | |
| 2017/0356517 A1 | 12/2017 | Betteridge et al. | |

\* cited by examiner

IMPACT ABSORBING PAD

CROSS-REFERENCE TO RELATED APPLICATIONS

This application claims priority from provisional U.S. Patent Application No. 62/020,486, filed Jul. 3, 2014, the disclosure of which is hereby incorporated herein by reference.

BACKGROUND OF THE INVENTION

The present invention relates to an impact absorbing pad, preferably for protection of a prosthetic implant during an implantation procedure.

Because of disease or injury, it may become necessary to replace an unhealthy bone structure with a prosthetic implant, such as a prosthetic knee or hip. For example, degenerative arthritis may cause the load bearing surfaces in a knee to deteriorate; thus requiring a knee arthroplasty procedure to relieve pain and restore mobility. Alternatively, a bone tumor might be discovered in the pelvis or femur; thus requiring a total or partial hip replacement surgery to remove the tumor. Whatever the case, during a typical replacement surgery, once the unhealthy bone structure is removed, an implant is required to restore and maintain bodily function.

Many implants require the installation of one or more components within a bone cavity, such as a bone stem. These implants are usually inserted into the bone cavity by force and then cemented in place. One benefit of such an implant is to provide a prosthetic, load bearing surface that is integral with the healthy bone structure. A prosthetic knee, for example, may include a flat baseplate with a bone stem that is inserted into and cemented to the tibia. The flat baseplate is typically a load bearing surface configured to receive a round ended implant that mimics the natural shape of a knee joint. Likewise, a prosthetic hip may comprise a ball rigidly attached to the femur. The ball is typically received in a socket having a load bearing surface that replicates the range of motion provided by a healthy hip.

Depending upon surgical approach and/or patient anatomy, the installation of a prosthetic implant may require the use of an impactor tool for driving the implant into place (e.g., driving a bone stem into a bone cavity). Because the impactor tool is generally not implanted within the body, it need not be constructed from a biocompatible material, such as titanium. Moreover, to improve durability and wear resistance of the striking surfaces, such tools are often plated with hard chrome. As a result, the load bearing surfaces of an implant can be burnished, indented, notched, or otherwise damaged by the repeated impactions required for implantation. Therefore, a need exists for a structure that can protect the load bearing surface of a prosthetic implant during implantation.

BRIEF SUMMARY OF THE INVENTION

A first aspect of the present invention is an impact absorbing pad adapted to protect a load bearing surface of an implant. The pad may be configured to absorb a portion of any impaction forces applied to the load bearing surface by the striking surface of an impactor tool. An exemplary pad may have a planar portion and an attachment portion. The attachment portion preferably attaches the pad to a portion of the implant.

In accordance with this first aspect, the attachment portion may be located on a perimeter of the pad. For example, the pad may have at least one tab on the perimeter that is configured to engage an attachment surface on the implant, such as a protrusion or ledge adjacent to the load bearing surface. If multiple tabs are deployed, then the implant may have multiple attachment surfaces for this purpose, each attachment surface being configured to engage one of the multiple tabs. The perimeter of the pad may also promote attachment with implant. For example, the pad may have a perimeter with an open shape having an exterior peripheral curve and an interior peripheral curve such that the perimeter is sized to surround a center section of the load bearing surface.

Other features of the pad may promote detachment from the implant. For example, if the open shape of the pad has a U-shaped perimeter with two prongs, then a fourth tab may span between the terminal ends of the two prongs so as to close the open shape. A bounded opening may thus be formed in the pad. The bounded opening may be adapted to surround a center portion of the implant. This fourth tab may be pulled to detach the pad from the implant. In some embodiments, the fourth tab may be bent or angled away from the planar portion to make it easier to grip. Still other features of the pad may be configured to enhance its impact absorbing capabilities. For example, the thickness or material composition of the pad may vary.

A second aspect of the present invention is a prosthetic insertion system that may include an implant having a load bearing surface, an impactor tool having an impaction surface at one end and a striking surface at the other end, and an impact absorbing pad. The striking surface of the impactor tool is preferably utilized to drive a portion of the implant into a bone stem when an impaction force is applied to the impaction surface. In use, the impact absorbing pad is preferably disposed between the load bearing surface of the implant and the striking surface of the impactor tool. This arrangement desirably allows any impaction forces applied to the impaction surface of the impactor tool to be transmitted to the implant through the pad. Preferably, at least a portion of these impaction forces are absorbed or dispersed by the pad.

A third aspect of the present invention is a method for using an impact absorbing pad. An exemplary step in this method may include preparing an implantation area of a patient, such as an area proximate to the knee. An implant with a load bearing surface attached to an impact absorbing pad may be positioned proximate to the implantation area. The striking surface of an impactor tool may be positioned adjacent the impact absorbing pad. Once the impactor tool is positioned, then an impaction force may be applied to an impaction surface of the tool and transmitted through the tool to the striking surface so as to drive a portion of the implant into a bone stem. Completion of these steps allows the impaction force to be transmitted through the pad to the load bearing surface of the implant without damaging the load bearing surface. In some embodiments, the impact absorbing pad is removed.

Various features of an impact absorbing pad may be configured in accordance with this third aspect. For example, the pad may have an attachment portion configured to removably attach the pad to the load bearing surface. This configuration desirably allows the implant to be assembled together with the pad. In some embodiments, the attachment portion comprises at least one tab on a perimeter of the pad. A portion of the impactor tool may also be attached to the implant. In other embodiments, a portion of the tab may be captured by the impactor tool when the tool is attached to the implant so that the pad is removable with the tool.

A fourth aspect of the present invention is a method of manufacturing an impact absorbing pad. An exemplary method step may comprise providing a stamping tool. The stamping tool may, for example, have a perimeter, a bladed surface, an application surface opposite of the bladed surface, and at least one tabular offshoot. A metal plate with a groove for receiving the bladed surface is provided so that a sheet of material may be inserted between the bladed surface and the groove. With the sheet inserted, a force may be applied to the application surface of the cutting tool so as to compel the bladed surface through the sheet and into the groove. The at least one tabular offshoot may have a bending rod that is contiguous with the perimeter and proximate to the bladed surface. Accordingly, the tab may be formed by bending the portions of the sheet contained in the at least one tabular offshoot over the bending rod.

DETAILED DESCRIPTION

The present invention is directed to different embodiments of an impact absorbing pad. Although the embodiments depicted in FIGS. 1-5 are designed for use with implants in the form of a prosthetic knee implant with a planar load bearing surface, it should be understood that other embodiments may be utilized with other types of implants having non-planar load bearing surfaces. For instance, it is well within the scope of the present application to provide an impact absorbing pad for use with any total or partial hip replacement implant having a curved loading bearing surface.

Figure 1:
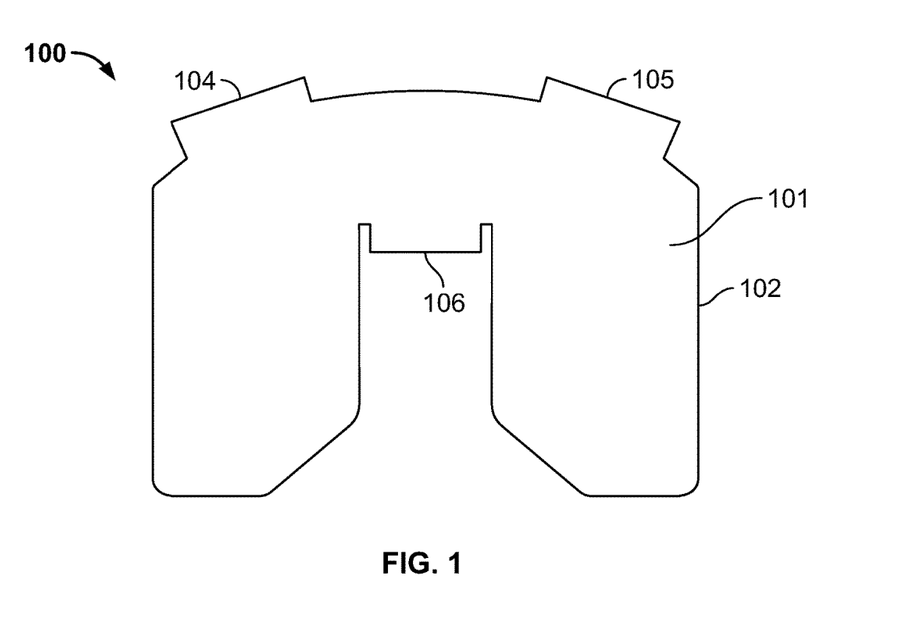
FIG. 1 is a top view of one embodiment of an impact absorbing pad in accordance with the present invention.
Figure 4:
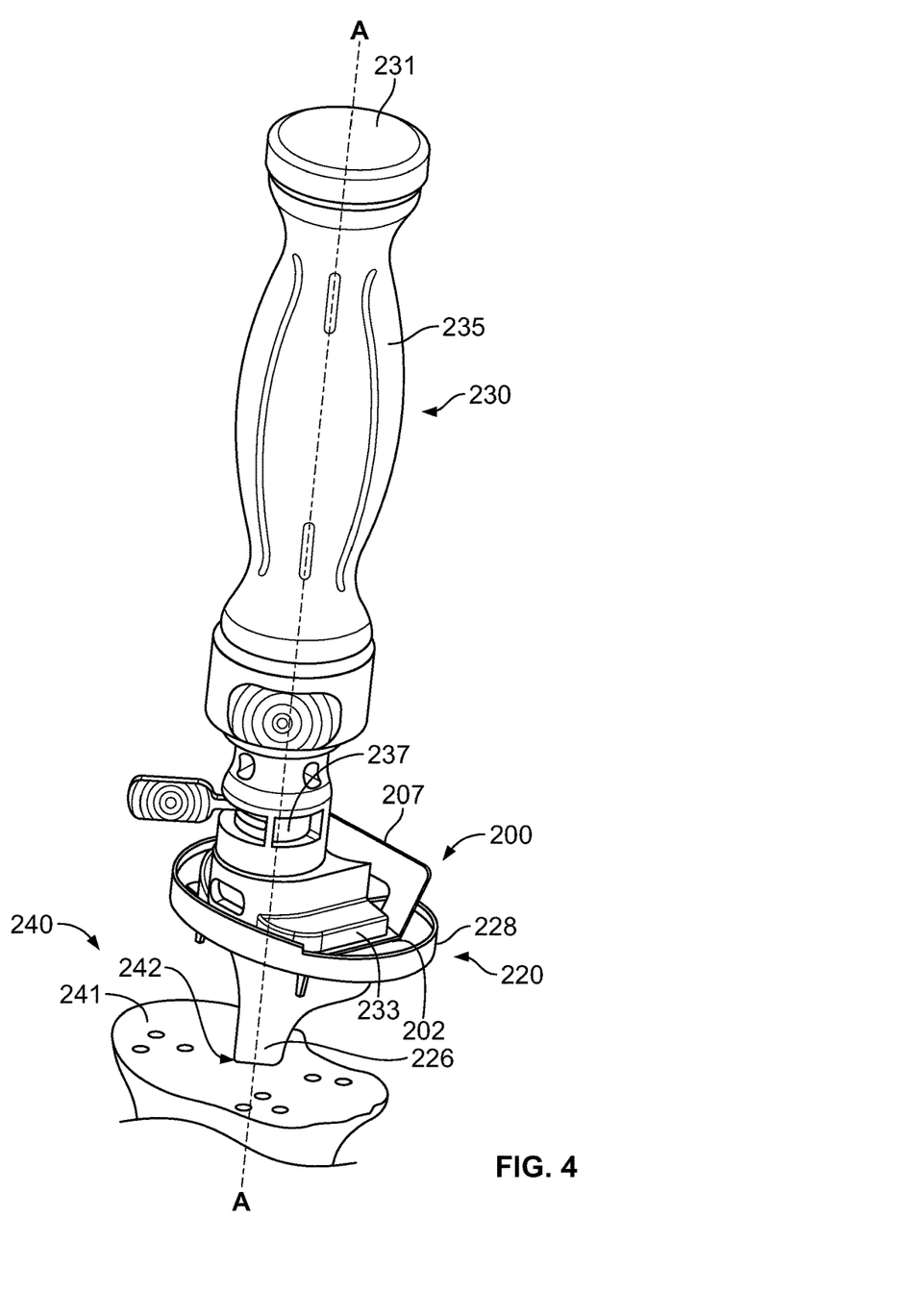
FIG. 4 is a perspective view of the impact absorbing pad and implant shown in FIG. 3 attached to an impactor tool.

A first embodiment impact absorbing pad 100 is depicted in FIG. 1. Pad 100 has a substantially planar portion 101 with an outer perimeter 102 that preferably corresponds to a load bearing surface 128 of an implant 120 (FIG. 2) and a striking surface 233 of an impactor tool 230 (FIG. 4). As described below, tool 230 may be used for the final implantation of a prosthetic knee into a tibia, wherein planar portion 101 of pad 100 is placed between load bearing surface 128 and striking surface 233. In some embodiments, the outer perimeter 102 of pad 100 may have an open shape that is, for example, defined by an exterior peripheral edge offset from an interior peripheral edge. Pad 100 is depicted in FIG. 1 with a substantially U-shaped perimeter that corresponds with the shape of load bearing surface 128. Preferably, pad 100 is contained within an inner perimeter 121 of implant 120, as in FIG. 2, so as to reduce material costs and further ensure that pad 100 remains attached to the implant throughout its shelf life and during implantation. Of course, depending upon the mode of attachment, the coverage and size of pad 100 may be increased to maximize its protective capabilities. For example, the size of pad 100 may be increased to protect any portion of implant 120 that is adjacent to load bearing surface 128.

Figure 2:
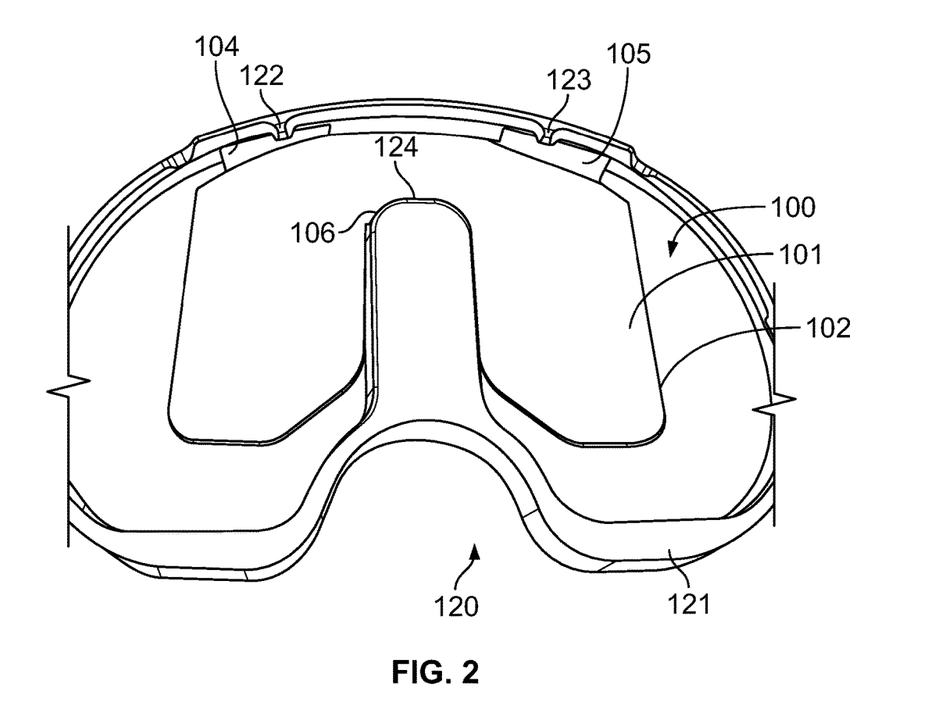
FIG. 2 is a perspective view of the impact absorbing pad shown in FIG. 1 attached to a load bearing surface.

Pad 100 of FIG. 1 may be a single-use device that is attached to implant 120 by the manufacturer and then removed by the surgeon during or after implantation. Accordingly, pad 100 preferably has an attachment portion configured to attach pad 100 to implant 120. In FIG. 1, said attachment portion comprises two peripheral tabs 104 and 105 and a center tab 106. As shown in FIG. 2, tabs 104 and 105 correspond with two peripheral attachment surfaces 122 and 123 on implant 120, while center tab 106 corresponds with a center attachment surface 124 of implant 120. In some embodiments, tabs 104, 105, and 106 are arranged triangularly about the perimeter 101 of pad 100, as in FIGS. 1 and 2. Pad 100 could alternatively have a single peripheral tab 104, or like structure, as described below.

Engaging tabs 104, 105, and 106 with attachment surfaces 122, 123, and 124 attaches pad 100 to implant 120, preferably in a non-permanent or removable fashion. Tabs 104, 105, and 106 are preferably formed integrally with the planar portion 101 of pad 100. Each tab may be bent about outer perimeter 102 until the longitudinal axis of each tab is transverse with planar portion 101. As shown in FIG. 2, for example, peripheral tabs 104 and 105 are bent to engage peripheral attachment surfaces 122 and 123, while center tab 106 is bent to engage inner attachment surface 124. Essentially, the positioning and bending of tabs 104, 105 and 106, and their subsequent engagement with attachment surfaces 122, 123 and 124, acts to hold pad 100 in a substantially fixed position relative to load bearing surface 128.

Although not shown, other non-permanent means of attaching pad 100 to implant 120 are also contemplated. For example, tabs 104, 105 and 106 may be omitted if the attachment portion of pad 100 is configured to be snap-fit with implant 120. In this embodiment, planar portion 101 of pad 100 may be sized to cover the entire loading bearing surface 128 of implant 120 and certain surrounding surfaces. For example, pad 100 may alternatively have a pad edge that extends away from planar portion 101 along perimeter 102. A channel may be formed on the interior or exterior surface of the pad edge. In complement, implant 120 may have an implant edge that extends away from load bearing surface 128 along perimeter 121 and a lip that extends outwardly from the interior or exterior surface of the implant edge. Accordingly, pad 100 may be snap-fit over or into a portion of implant 120 when the lip on the implant edge is received in the channel on the pad edge. Alternatively, the attachment portion of pad 100 may be a continuous tab that runs around perimeter 102 of planar portion 101. An implant 120, similar to above, may have a continuous implant edge extending away from load bearing surface 128 along perimeter 121 and a continuous lip extending inwardly from the edge. In this embodiment, pad 100 is snap-fit into implant 120 when the continuous tab of pad 100 is bent under the continuous lip of implant 120. Alternatively still, any portion pad 100 may be non-permanently attached to implant 120 by use of an adhesive, such as a biocompatible, low-tack adhesive or the like. In this regard, the attachment portion of pad 100 may comprise any surface of pad 100 that has been coated with the adhesive, such as either side of planar portion 101.

Any embodiment of pad 100 may be attached to an implant 120 in a more permanent manner. For example, a biocompatible embodiment of pad 100 may be attached to load bearing surface 128 and then implanted into the body with implant 120. This embodiment of pad 100 may be attached to implant 120 in any manner. Planar surface 101 of pad 100 may be further configured to protect load bearing surface 128 when in use. For example, when utilized in a knee implant, pad 100 may be used to disperse the weight of the body and reduce friction between a rounded edge knee implant and load bearing surface 128, much like the lateral and medial meniscus of a knee. Alternatively still, a load bearing insert (not shown) may be placed over pad 100 and then secured to implant 120 after implantation. Said insert may be used to ensure that load bearing surface 128 is pristine after implantation. The loading bearing insert may, for example, have one or more tabs or surfaces that are engageable with any of the attachment surfaces 122, 123, and 124 of implant 100 to secure pad 100 between the insert and load bearing surface 128. In this regard, pad 100 may both protect implant 100 during implantation and serve as a securing or dampening element when in use.

Pad 100 has also been described as being attached to implant 120. Another embodiment of pad 100 may be attached to impactor tool 230. For example, an attachment portion of pad 100, like tabs 104, 105, or 106, may be attached directly to a portion of impactor tool 230 so as to position the planar surface 101 of pad 100 between striking surface 233 of tool 230 and load bearing surface 128 of implant 120, as described above. In some embodiments, the configuration of tabs 104, 105, and 106 and a corresponding set of attachment surfaces on either implant 120 and tool 230 are configured so that pad 100 may be interchangeably attached to either implant 120 or impactor tool 230.

Pad 100 is preferably made from a homogeneous polymeric material that can be optimized for biocompatibility, durability, and manufacturing tolerances. By way of example, pad 100 may be between approximately 0.001 and 0.010 inches thick, or between approximately 0.010 and 0.020 inches, or thicker or thinner, depending upon the material type. For example, pad 100 is preferably manufactured from a 0.002 inch thick sheet of polyether ether ketone ("PEEK"). In some embodiments, portions of pad 100 may be thicker than others, such as those portions adjacent striking surface 233 of tool 230; or, for example, those portions adapted to receive the rounded edges of a knee implant when pad 100 is attached to implant 120.

Any portion of pad 100 may also manufactured from any number alternate polymeric materials, such as amorphous polyethylene terephthalate ("APET"), polyethylene terephthalate glycol-modified ("PETG"), polystyrene ("HIPS"), polyphenylene sulfide ("PPS"), polyethersulfone ("PESU"), Low Density Polyethylen (LDPE), Polyether Polyurethane ("Stevens"), or a heterogeneous combination of these or similar materials. Of course, one skilled in the art would recognize that pad 100 may also be manufactured from any non-petroleum or non-polymeric material with comparable properties. For example, pad 100 might alternatively be manufactured from an organic plastic, such as those derived from polylactic acid or like materials.

In yet another embodiment, pad 100 may alternatively be manufactured from a layered combination of materials. For example, a first surface of pad 100 oriented away from load bearing surface 128 (a "cranial surface") may consist of at least one layer of polymeric material, while a second surface of pad 100 oriented oppositely towards surface 128 (a "caudal surface") consists of at least one layer of impact absorbing material, such as organic cotton. Either of the cranial or caudal surfaces may be smoothed, patterned, or dimpled to provide further impaction force dispersion. For example, the caudal surface may have a waffled surface with shaped indentions dispersed throughout to create air pockets that further distribute impact energy. As a further example, the cranial surface may be formed of a denser material to facilitate the attachment of pad 100 with impactor tool 230. Alternatively still, a layer of pressure reactive, magnetic, or other sensory responsive material may be inserted between or integrated with the cranial and caudal surfaces. These layers may impart pad 100 with additional capabilities, such as magnetic attachment to implant 120 or the ability to provide the surgeon with sensory or tactile feedback during implantation. The thickness of pad 100 may be varied to promote these additional capabilities.

Figure 3:
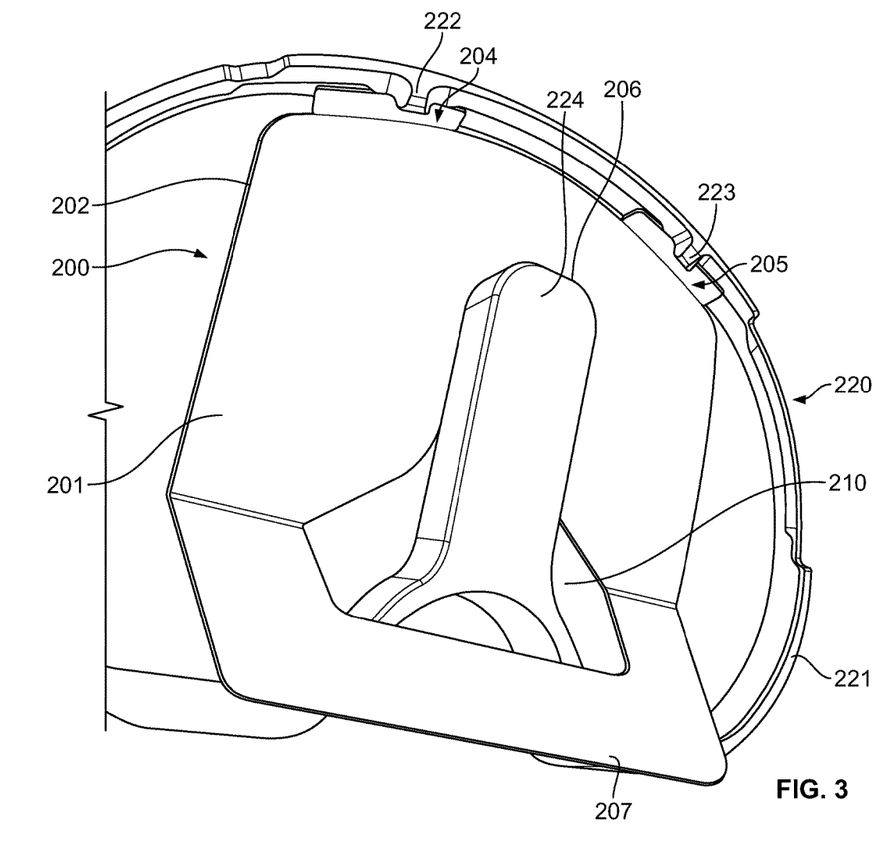
FIG. 3 is a top view of an alternate embodiment of an impact absorbing pad attached to another load bearing surface.

An alternate embodiment of impact absorption pad 100 is depicted in FIGS. 3 and 4 as a pad 200. Where similar components to those of pad 100 are included in pad 200, similar reference numerals are utilized, but within the 200 series of numbers. For instance, pad 200 of FIG. 3 has a substantially planar portion 201 with an attachment portion having a trio of tabs 204, 205, and 206, each tab being configured to engage one of a corresponding trio of attachment surfaces 222, 223, and 224 on an implant 220. In contrast to above, however, pad 200 further comprises a posterior or removal tab 207 forming a bounded opening 210 within pad 200. Posterior tab 207 provides an additional means for detaching pad 200 from implant 220. For example, pad 200 may be attached to implant 220 during a manufacturing process. In some embodiments, pad 200 will remain attached during implantation until it is removed by application of a pulling force to posterior tab 207. The pulling force is preferably applied directly to posterior tab 207, such that pad 200 is removed by hand. This is in contrast to pad 100, which may require a removal tool. Alternatively, posterior tab 207 may be captured by a portion or surface of impactor tool 230 so that detaching tool 230 from implant 220 also removes pad 200.

A method of using impact absorption pad 100 or 200 is now described with particular reference to pad 200 of FIG. 4. As illustrated, FIG. 4 provides a perspective view of pad 200, implant 220, and impactor tool 230 in an assembled state. A bone 240 with an implantation surface 241 is also depicted. Impactor tool 230 has an impaction surface 231 opposite of a striking surface 233 along a longitudinal axis A-A of tool 230. In one step, impactor tool 230 may be assembled with implant 220 so as to position planar surface 101 of pad 200 between a striking surface 233 of tool 230 and a load bearing surface 228 of implant 220. This step may include attaching pad 200 to surface 228, as described above. Another method step may comprise preparing implantation surface 241, for example, by forming a bone cavity 242 therein.

After implantation surface 241 has been prepared, a portion of implant 220 is positioned proximately thereto. For example, FIG. 4 depicts impactor tool 230 as being used to place a bone stem 226 of implant 220 proximate to cavity 242. Once implant 220 has been positioned, an impaction force is preferably applied to impaction surface 231 of tool 230 along its longitudinal axis A-A. Tool 230 is preferably adapted to transmit the impaction force along axis A-A from impaction surface 231, through a tool body 235, to striking surface 233, and then through pad 200 to load bearing surface 228 so as to drive bone stem 226 into bone cavity 242. By utilizing this method, pad 200 may attached to implant 220 such that any impaction forces applied by tool 230 are transmitted through pad 200 to implant 220 without damaging load bearing surface 228.

Additional method steps may be required to remove pad 100 or 200. For example, tool 230 may be detached from implant 220 and then moved away from implantation site 241 after bone stem 226 has been driven into cavity 242. A pulling force may then be applied to posterior tab 207 of pad 220 to remove pad 220 from implant 220. Alternatively, an attachment mechanism 237 of impactor tool 230 may be operated to attach a portion or surface of tool 230 to implant 220, thus requiring impactor tool 230 to be detached from implant 120 and removed prior to removing pad 220. For example, mechanism 237 may comprise a clamp operated by a lever, the clamp being adapted to grip the center section of load bearing surface 128 when the lever is moved from an unlocked to a locked position. Accordingly, this method may further comprise moving the lever to detach tool 230 from load bearing surface 128, moving tool 230 away from implant 120, and removing pad 210. Alternatively still, a portion of posterior tab 207 may be captured by tool 230 so that removing tool 230 also removes pad 200. For example, a portion of center tab 206 may be caught in the clamp or hooked on the lever. A similar method to the foregoing would apply to pad 100 and implant 120, with the lack of tab 207 largely being the difference. In the case of pad 100, a secondary, clip or plier-like tool (not shown) is preferably utilized within a step for removing the pad from the implant.

Figure 5:
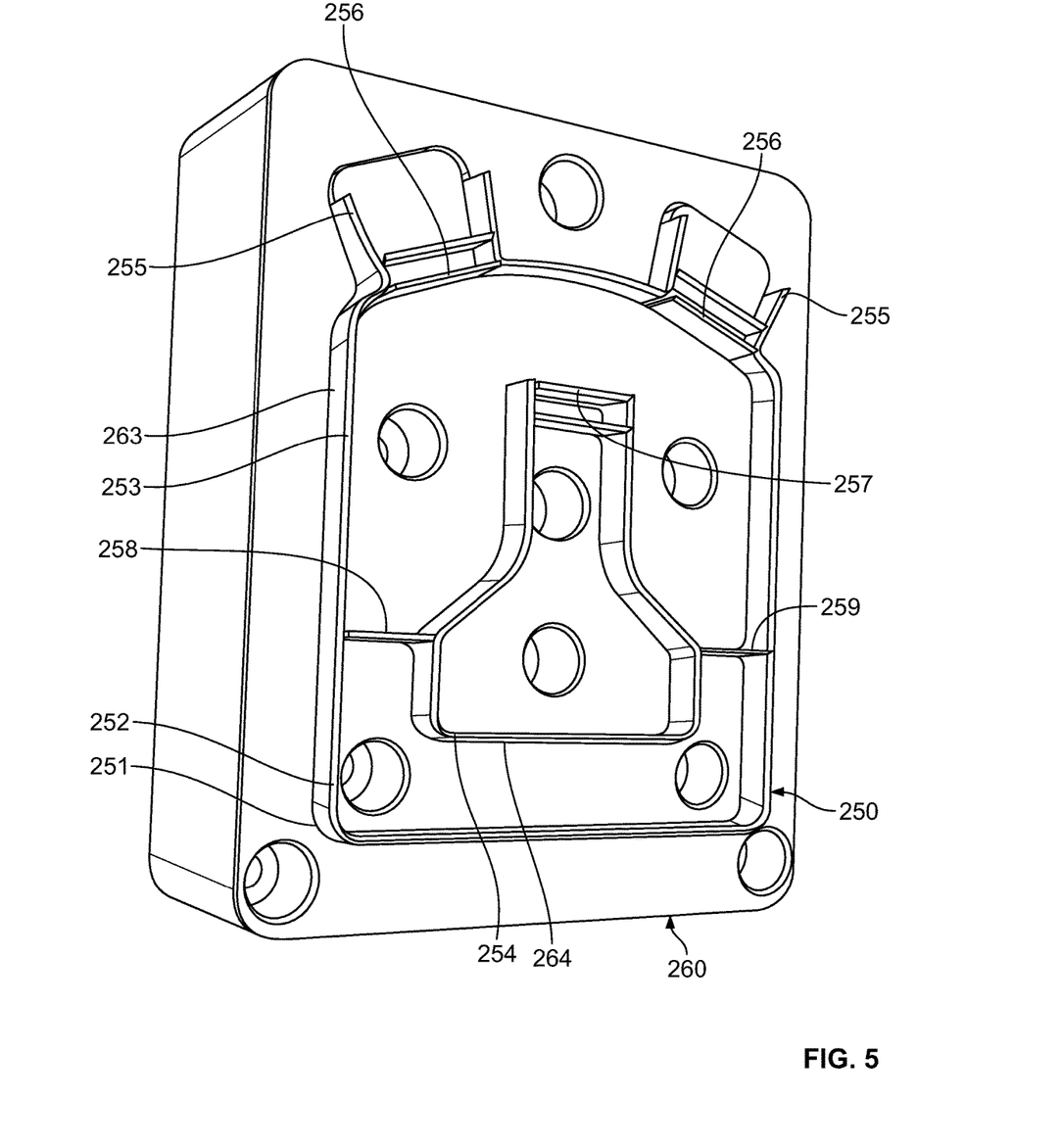
FIG. 5 is a perspective view of a tool used to manufacture the impact absorbing pad shown in FIG. 3.

A method of manufacturing pad 200 is also disclosed with reference to FIG. 5, although a similar method could be applied to any embodiment of pad 100. FIG. 5 shows a stamping tool 250 and a plate 260. Stamping tool 250 comprises a bladed surface 251 (shown embedded within plate 260) and an application surface 252 opposite of bladed surface 251. Bladed surface 251 has an outer bladed perimeter 253, an inner bladed perimeter 254, at least one tabular offshoot 255 forming the tab perimeter, at least one peripheral bending rod 256, a center bending rod 257, and two posterior bending rods 258 and 259. Plate 260 has an outer groove 263 corresponding with outer bladed perimeter 253 of tool 250; and an inner groove 264 corresponding with inner bladed perimeter 254 of tool 250.

Preferably, a thin sheet of PEEK (not shown), or like material, including any of those enumerated above, is inserted between stamping tool 250 and plate 260. A force is then applied to a portion of application surface 252 to compel the inner and outer bladed perimeters of bladed surface 251 into the corresponding outer and inner grooves 263 and 264 of plate 260 until impactor pad 200 is cut from the thin sheet of PEEK. Each of the respective peripheral tabs 204 and 205, center tab 206, and posterior tab 207 are then bent around their corresponding peripheral bending rods 256, center bending rod 257, and the two posterior bending rods 258 and 259. After which, stamping tool 250 is moved away from plate 260 so that pad 220 may be removed.

Additional manufacturing steps may be included to accommodate any embodiment of pads 100 or 200 described in this application. For example, the above steps may be modified to accommodate a sheet of any material or thickness described herein. An additional manufacturing step may comprises, as a further example, applying a layer of material to either the cranial or caudal surface of pad 100 or 200, such as the adhesives or impact absorbing materials described above. Such layers may be applied to the sheet of material before or after the pad is formed. Either surface of pads 100 or 200 may also undergo additional finishing steps, such as etching, molding, stamping or like processes, so as to achieve any of the surface features described above. Alternatively, the thin sheet of material may be finished in advance so that pad 100 may be cut from a sheet of material having said additional layers or surface features. Still other manufacturing steps may be required for manufacturing an implantable embodiment of pad 100. For example, any embodiment of pad 100 may be sterilized, attached to either implant 120 or tool 230, and then sealed within a kit for implantation at a later date. Said kits may include a plurality of pads 100, implants 120, or tools 230, depending upon type of implant and intended usage.

Although the invention disclosed in this application has been described with reference to particular embodiments, it is to be understood that these embodiments are merely illustrative of the principles and applications of the present invention. Accordingly, numerous modifications may be made to the illustrative embodiments, and other arrangements may be devised, without departing from the spirit and scope of the invention disclosed in this application.

The invention claimed is:

1. An impact absorbing pad comprising:
 a substantially planar portion including a first substantially planar surface having a first surface area defined by a perimeter and a second substantially planar surface having a second surface area substantially the same as the first surface area, the second substantially planar surface opposite the first substantially planar surface, wherein the perimeter corresponds with a shape of a load bearing surface of an implant and includes an exterior peripheral edge and an interior peripheral edge; and
 an attachment portion that is integral with the substantially planar portion and configured to removably attach the substantially planar portion to the load bearing surface of the implant, the attachment portion including one or more peripheral tabs on each of the exterior and interior peripheral edges, the peripheral tabs being integral with the substantially planar portion, wherein the one or more peripheral tabs on the interior peripheral edge is located interior to the exterior peripheral edge and in between a width of the substantially planar portion measured between opposing sides of the exterior peripheral edge,
 wherein the attachment portion is movable relative to the substantially planar portion.

2. The pad of claim 1, wherein the substantially planar portion is configured to absorb at least a portion of any impaction forces applied thereto.

3. The pad of claim 1, wherein the impact absorbing pad is between approximately 0.001 and approximately 0.020 inches thick.

4. The pad of claim 1, wherein the substantially planar portion is made of at least one layer of polymeric material.

5. The pad of claim 1, wherein the perimeter is substantially U-shaped.

6. The pad of claim 5, wherein the one or more peripheral tabs on the interior peripheral edge is located remote from terminal ends of the U-shape.

7. The pad of claim 1, further comprising a removal tab spanning between a first terminal end and a second terminal end of the perimeter of the first substantially planar surface such that the one or more peripheral tabs on the interior peripheral edge is fully enclosed by the combination of the substantially planar portion and the removal tab.

8. The pad of claim 1, wherein the one or more peripheral tabs on each of the exterior and interior peripheral edges comprises a first tab and a second tab on the exterior peripheral edge and a third tab on the interior peripheral edge, the first, second, and third tabs being arranged triangularly on the perimeter.

9. The pad of claim 4, wherein the substantially planar portion is made of two layers of material including the at least one layer of polymeric material and a second layer made of a material different than the at least one layer.

10. An impact absorbing pad comprising:
a substantially planar portion including a first substantially planar surface having a first surface area defined by a perimeter and a second substantially planar surface having a second surface area substantially the same as the first surface area, the second substantially planar surface opposite the first substantially planar surface, wherein the perimeter corresponds with a shape of a load bearing surface of an implant and includes an exterior peripheral edge and an interior peripheral edge; and
an attachment portion that is integral with the substantially planar portion and configured to removably attach the substantially planar portion to the load bearing surface of the implant, the attachment portion including one or more peripheral tabs on each of the exterior and interior peripheral edges, the peripheral tabs being integral with the substantially planar portion; and
a removal tab spanning between a first terminal end and a second terminal end of the perimeter of the first substantially planar surface, the perimeter being substantially U-shaped, such that the one or more peripheral tabs on the interior peripheral edge is fully enclosed by the combination of the substantially planar portion and the removal tab,
wherein the attachment portion is movable relative to the substantially planar portion.

11. A prosthetic insertion system comprising:
an implant having a load bearing surface;
an impactor tool having a striking surface; and
an impact absorbing pad having a substantially planar portion and an attachment portion that is integral with the substantially planar portion, the attachment portion configured to removably attach the substantially planar portion to the load bearing surface of the implant,
wherein the substantially planar portion includes a first substantially planar surface having a first surface area defined by a perimeter and a second substantially planar surface having a second surface area substantially the same as the first surface area, the second substantially planar surface opposite the first substantially planar surface, the perimeter corresponding with a shape of the load bearing surface of the implant and including an exterior peripheral edge and an interior peripheral edge,
wherein the attachment portion includes one or more peripheral tabs on each of the exterior and interior peripheral edges, the peripheral tabs being integral with the substantially planar portion, the one or more peripheral tabs on the interior peripheral edge located interior to the exterior peripheral edge and in between a width of the substantially planar portion measured between opposing sides of the exterior peripheral edge,
wherein any impaction forces applied to the striking surface of the impactor tool are transmitted through the substantially planar portion of the impact absorbing pad to the load bearing surface of the implant when the impact absorbing pad is attached to the load bearing surface, and
wherein the attachment portion is movable relative to the substantially planar portion.

12. The system of claim 11, wherein the attachment portion is proximate to the perimeter of the first substantially planar surface.

13. The system of claim 11, wherein the implant has at least one attachment surface engageable with each of the one or more peripheral tabs on each of the exterior peripheral edge and the interior peripheral edge.

14. The system of claim 11, wherein the one or more peripheral tabs on each of the exterior and interior peripheral edges comprises a first tab and a second tab on the exterior peripheral edge and a third tab on the interior peripheral edge.

15. The system of claim 14, wherein the first, second, and third tabs are arranged triangularly on the perimeter.

16. The system of claim 15, wherein the impact absorbing pad has a U-shaped perimeter with two prongs such that the exterior peripheral edges are exterior of each prong and the interior peripheral edges are interior of each prong.

17. The system of claim 16, further comprising a removal tab spanning between a terminal end of each of the two prongs so as to define a bounded opening within the impact absorbing pad, and wherein the impact absorbing pad may be detached from the implant by applying a pulling force to the removal tab.

* * * * *